United States Patent
Fukushima et al.

(10) Patent No.: US 6,787,673 B2
(45) Date of Patent: Sep. 7, 2004

(54) PROCESS FOR PRODUCING 2-BROMOCYCLOPENTANONE

(75) Inventors: Daisuke Fukushima, Tsukuba (JP); Norihiko Hirata, Suita (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/700,694

(22) Filed: Nov. 4, 2003

(65) Prior Publication Data

US 2004/0138505 A1 Jul. 15, 2004

(30) Foreign Application Priority Data

Nov. 8, 2002 (JP) ...................................... 2002-324989

(51) Int. Cl.$^7$ ............................................. C07C 45/00
(52) U.S. Cl. ........................ 568/348; 358/364; 358/380
(58) Field of Search ................................ 568/348, 364, 568/380

(56) References Cited

U.S. PATENT DOCUMENTS

| | | | | | |
|---|---|---|---|---|---|
| 2,466,681 A | * | 4/1949 | Bruson et al. | ............... | 568/348 |
| 2,667,512 A | * | 1/1954 | Adelson | ................. | 568/346 |
| 3,355,493 A | * | 11/1967 | Anello et al. | ............... | 568/348 |
| 4,217,251 A | * | 8/1980 | Dastur | ............................ | 512/8 |
| 4,288,613 A | * | 9/1981 | Larock | ........................ | 560/231 |
| 6,500,990 B2 | * | 12/2002 | Asada et al. | ................. | 568/341 |

FOREIGN PATENT DOCUMENTS

| | | |
|---|---|---|
| JP | 60-028948 A | 2/1985 |
| JP | 2000-178220 A | 6/2000 |
| JP | 2000-256387 A | 9/2000 |

OTHER PUBLICATIONS

Lau, C.K., et al., "Evolution of a Series of Non–Quinoline Leukotriene D$_4$ Receptor Antagonist; Synthesis and SAR of Benzothiazoles and Thiazoles Substituted Benzyl Alcohols as Potent LTD$_4$ Antagonists", *Bioorganic & Medicinal Chemistry Letters*, vol. 5, No. 15, pp. 1615–1620 (1995).

Chande, M.S., et al., "Synthesis of New 3–Substituted Cycloalkylo(e)–s–Triazolo (3,4–b)(1,3,4) Thiadiazines as Potential Antimicrobial and Antiparasitic Agents", *Indian J. Heterocyclic Chemistry*, vol. 1, pp. 117–120 (1991).

Huang, W., et al., "Reactions of Perfluoroalkanesulfonyl Bromide", *Bulletin de la Société Chimique de France*, No. 6, pp. 881–884 (1986).

Baasov, T., et al., "Model Compounds for the Study of Spectroscopic Properties of Visual Pigments and Bacteriorhodopsin", *J. Am. Chem. Soc.*, vol. 107, pp. 7524–7533 (1985).

Stanovnik, B., et al., "3–Bromoimidazol[1,2–b]pyridazine––Bromine and 3–Bromo–6–chloroimidazol[1,2–b]pyridazine–Bromine Complexes; New Brominating Agents for Organic Compounds", *Synthesis*, pp. 987–989 (Dec. 1981) E. Kardelj Univ. of Ljubljana, Yugoslavia.

Olah, G., et al., "Synthetic Methods and Reactions 73[1] Conversion of Epoxides and Enamines into α–Haloketones with Halodimethylsulfonium Halides", *Tetrahedron Letters*, No. 38, pp. 3653–3656 (1979).

Lazukina, L.A., et al., "Reactions of Trimethyl(vinyloxy)silanes with Halogens, Cyanogen Bromide, and Thiocyanogen", *Institute of Organic Chemistry, Academy of Sciences of the Ukrainian SSR*, vol. 45, No. 9, p. 2100 (Sep. 1975).

Hiroi, K., et al., "Sterochemical Studies. XX.[1)] Asymmetric Synthesis of α–Bromoketones", *Chem. Pharm. Bull.*, vol. 21, No. 1, pp. 54–61 (1973).

* cited by examiner

*Primary Examiner*—Amelia A. Owens
(74) *Attorney, Agent, or Firm*—Akin Gump Strauss Hauer & Feld, LLP

(57) ABSTRACT

There is provided a process for producing 2-bromocyclopentanone which process is characterized in that cyclopentanone is reacted with bromine in a biphasic mixture of water and an organic solvent.

8 Claims, No Drawings

PROCESS FOR PRODUCING 2-BROMOCYCLOPENTANONE

FIELD OF THE INVENTION

The present invention relates to a process for producing 2-bromocyclopentanone, which is a useful intermediate for the production of pharmaceuticals.

BACKGROUND OF THE INVENTION

It is disclosed in the Experimental section of Indian J.Heterocycl.Chem., 1991, 1 (3) 117 that a reaction of bromine with cyclopentanone in chloroform gave 2-bromocyclopetanone in a yield of 36%. J. Amer. Chem. Soc., 1985, 107 (25), 7524 discloses a bromination reaction of cyclopetanone using N-bromosuccinimide as a brominating agent, and Synthesis 1981, (12) 987 discloses, as a brominating agent, a bromine complex with an imidazo [1,2-b] pyrldadine derivative. Zh.Obshch.Khim., 1975, 45(9),2100 and Chem.Pharm.Bull., 1973, 21(1), 54 disclose bromination reactions of cyclopentanone enol or enamine with bromine respectively. Since the yield of the first process is not satisfactory and the latter processes required expensive brominating agent and derivatization steps to produce cyclopentanone enol or enamines from cyclopentanone, they are not always satisfactory for an industrial scale of production.

DETAILED DESCRIPTION OF THE INVENTION

According to the present invention, 2-bromocyclopentanone can be advantageously produced in an industrial scale of production.

The present invention provides a process for producing 2-bromocyclopentanone which comprises reacting cyclopetanone with bromine in a biphasic mixture of (i) water and (ii) an organic solvent or mixtures thereof.

2-Bromocyclopentanone is produced, for example, typically by dropwise-addition of bromine to a mixture of a biphasic mixture of water and the organic solvent, and cyclopentanone.

Cyclopentanone is usually used in such an amount that the molar ratios of cyclopentanone to bromine are 20:1 to 1:1, and preferably 10:1 to 1:1, and more preferably 5:1 to 2:1. The amount of water in the biphasic mixture is usually 0.1 to 100 parts by weight, preferably 0.5 to 20 parts by weight per one part by weight of bromine.

Examples of the organic solvent, as the component of the biphasic mixture comprising (i) water and (ii) an organic solvent or mixtures thereof, is typically a water immiscible organic solvent. The water immiscible organic solvent means an organic solvent that can form a biphasic mixture with water.

Specific examples of the organic solvent include, for example, halogenated hydrocarbons such as dichloromethane, dichloroethane, chloroform, 1-chlorobutane, or chlorobenzene;

ethers such as diethyl ether, a diisopropyl ether, tert-butyl methyl ether or the like;

aromatic hydrocarbons such as toluene, benzene, xylene or the like;

aliphatic hydrocarbons such as hexane, heptane or the like;

alcohols such as n-octanol, n-nonyl alcohol, n-decyl alcohol or the like;

esters such as ethyl acetate, butyl acetate, a methyl propionate or the like; and ketones such as methyl ethyl ketone, methyl isobutyl ketone, or the like. Preferred organic solvent that can form two phases with water is a water immiscible organic solvent that has no carbonyl group. More preferred are halogenated hydrocarbons, and still more preferred is 1-chlorobutane. The amount the organic solvent or mixtures thereof is usually in a range of from 0.1 to 100 parts by weight, preferably 0.5 to 20 parts by weight per one part by weight of bromine.

The addition of bromine is usually conducted at a range of from −10 to 80° C., preferably about 0 to 50° C. After completion of addition of bromine, the temperature is usually maintained thereafter. For example, after completion of the addition of bromine, the temperature is usually maintained for about 0.5 to 100 hours, preferably for 2 to 50 hours. The temperature after completion of the addition of bromine is usually maintained in the range of from −10 to 80° C., preferably about 0 to 50° C. 2-Bromocyclopentanone thus produced can be isolated by conventional methods. 2-Bromocyclopentanone can be isolated, for example, by separating oil phase and a water phase and evaporating the solvent of the oil phase containing 2-bromocyclopentanone. Unreacted cyclopetanone, if any, may be separated from 2-bromocyclopentanone by distillation. The recovered cyclopentanone can be reused in the present reaction. 2-Cyclopentanone thus obtained may be further purified by distillation, column chromatography or the like.

2-Bromocyclopentanone is, for example, suitably used to produce 2-cyclopentene-1-one by reacting 2-bromocyclopentanone with abase (dehydrobromonation reaction). Typical examples of the base include lithium carbonate, which is usually used in the co-presence of lithium bromide. Further specific conditions of the dehydrobromination reaction are referred to, for example, JP2000178220A. Thus produced 2-cyclopentene-1-one may be purified, if necessary, by distillation, column chromatography and/or the like.

According to the present invention, 2-bromocyclopentanone can be produced from cyclopentanone and bromine with good selectivity.

EXAMPLES

The present invention is further illustrated by means of Examples as below but are not to be construed to limit the invention thereto.

Example 1

40.0 g (250.3 mmol) of bromine was added to a mixture of 63.2 g (750.9 mmol) of cyclopentanone, 60.0 g of water and 60.0 g of 1-chlorobutane at 1° C. in 2 hours, and the resulting mixture was agitated at the temperature for 15 hours. After the completion of the agitation, 44.0 g of water, and 60.0 g of 1-chlorobutane were added thereto and agitated at the temperature for 15 minutes, and then the oil phase was separated from the water phase. 185.9 g of 1-chlorobutane solution containing 34.5 g (211.7 mmol, yield: 84.7% in terms of bromine) of 2-bromocyclopentanone was obtained as an oil phase. 2-Cyclopentylidenecyclopentanone was not found in this solution.

Example 2

40.0 g (250.3 mmol) of bromine was added dropwise at 1° C. to a mixture of 105.3 g (1251.5 mmol) of cyclopentanone, 60.0 g of water and 60.0 g 1-chlorobutane in 2 hours, and the resulting mixture was agitated at the temperature for 10 hours. After completion of the agitation, 44.0 g of water, and 60.0 g of 1-chlorobutane was added thereto and agitating at the temperature for 10 minutes, the oil phase was separated from the water phase. 228.2 g of 1-chlorobutane solution containing 33.8 g (207.4 mmol, yield: 82.8% in terms of bromine) of 2-bromocyclopentanone was obtained as an oil phase. 2-Cyclopentilydenecyclopentanone was not contained in this solution. Evaporation of this solution gave 37.0 g of a brownish solution containing 32.8 g (201.2 mmol, yield: 80.4% in terms of bromine) of 2-bromocyclopentanone. Unreacted cyclopentanone was collected as a distillate.

Example 3

20.0 g (125.1 mmol) of bromine was added to a mixture of 31.6 g (375.4 mmol) of cyclopentanone, 30.0 g of water and 30.0 g of hexane at 1° C. in 2 hours, and the resulting mixture was agitated at the temperature for 76 hours. After the completion of the agitation, 22.0 g of water, and 30.0 g of hexane were added and agitated at the temperature for 15 minutes, an oil phase-1 was separated from water phase-1. 50.0 g of hexane was added to the water phase-1 and agitated at 20° C. for 15 min and separated to give an oil phase-2 and a water phase. The oil phase-1 and the oil phase-2 were combined to give 135.6 g of a hexane solution containing 11.5 g (7.03 mmol, yield: 56.2% in terms of bromine) of 2-bromocyclopentanone. 2-Cyclopentylidenecyclopentanone was not found in this solution.

Example 4

40.3 g (252.2 mmol) of bromine was added to a mixture of 42.1 g (500.6 mmol) of cyclopentanone, 60.0 g of water and 60.0 g of 1-chlorobutane at 1° C. in 2 hours, and the resulting mixture was agitated at the temperature for 24 hours. After completion of the agitation, 44.0 g of water and 60.0 g of 1-chlorobutane were added thereto and agitated at the temperature for 15 minutes, and the oil phase and the water phase were separated. 168.6 g of 1-chlorobutane solution containing 32.4 g (198.5 mmol, yield: 78.7% in terms of bromine) of 2-bromocyclopentanone was obtained as the oil phase. 2-Cyclopentylidenecyclopentanone was not found in this solution.

Reference Example 1

40.0 g (250.3 mmol) of bromine was added dropwise to 105.3 g (1251. 5 mmol) of cyclopentanone at 1° C. in 2 hours, and agitated at the temperature for 80 hours. After completion of agitation, 105.3 g of water was added thereto and agitating at the temperature for 15 minutes, and separated a water phase to give 83.6 g of an oil phase containing 25.2 g (154.4 mmol, yield: 61.7% in terms of bromine) of 2-bromocyclopentanone and 7.5 g (50.0 mmol) of byproduct 2-cyclopentilydenecyclopentanone was obtained.

Reference Example 2

40.0 g (250.3 mmol) of bromine was dropwise added at 1° C. to a solution of 105.3 g (1251.5 mmol) of cyclopentanone in 120.0 g of 1-chlorobutane in 2 hours, and agitated at the temperature for 10 hours. After completion of the agitation, 105.3 g of water and was added thereto and agitated at the temperature for 15 minutes, and then 226.8 g of a solution containing 33.0 g (202.3 mmol, yield: 80.6% in terms of bromine) of 2-bromocyclopentanone and 7.3 g (48.4 mmol) of byproduct 2-cyclopentilydenecyclopentanone was obtained.

Example 5

21. 6 g of a reaction product, which was obtained in a similar manner as in Example 2 and containing 20.0 g (122.7 mmol) of 2-bromocyclopentanone, was added to a mixture of 60.0 g of N,N-dimethylformamide, 5.44 g (73.6 mmol) of lithium carbonate, 0.51 g (4.9 mmol) of lithium bromide monohydrate and 0.02 g (0.2 mmol) of hydroquinone in one hour at 100° C. under stirring, and maintained at the same temperature for 3 hours and then cooled to give a solution containing 9.3 g (113.0 mmol) of 2-cyclopentene-1-one (yield:92.1%). The obtained solution was distilled at 6.7 KPa and 50 to 120° C. to give 58.0 g of a solution of 9.2 g (112.6 mmol, yield based on 2-bromocyclopentanone: 91.8%) of 2-cyclopentene-1-one in N,N'-dimethylformamide.

What is claimed is:

1. A process for producing 2-bromocyclopentanone, which comprises reacting cyclopentanone with bromine in a biphasic mixture of (i) water and (ii) an organic solvent or mixtures thereof.

2. A process according to claim 1, wherein the organic solvent is a water immiscible organic solvent having no carbonyl group.

3. A process according to claim 1, wherein the organic solvent is halogenated hydrocarbon, hydrocarbon or mixtures of halogenated hydrocarbon and hydrocarbon.

4. A process according to claim 1, wherein the organic solvent is halogenated hydrocarbon.

5. A process according to claim 3, wherein the halogenated hydrocarbon is 1-chlorobutane.

6. A process according to claim 1, wherein the molar ratio of cyclopentanone to bromine is 10:1 to 1:1.

7. A process according to claim 1, wherein the molar ratio of cyclopentanone to bromine is 5:1 to 2:1.

8. A process according to claim 1, which further comprises the step of reacting 2-bromocyclopentanone with a base to produce 2-cyclopentene-1-one.

* * * * *